United States Patent
Fang et al.

(10) Patent No.: US 12,315,207 B2
(45) Date of Patent: May 27, 2025

(54) AUTOMATIC IDENTIFICATION METHOD, APPARATUS AND DEVICE FOR DETECTION RESULTS OF IMMUNOREAGENT CARD

(71) Applicant: Zhejiang Orient Gene Biotech Co., Ltd, Zhejiang (CN)

(72) Inventors: Jianqiu Fang, Zhejiang (CN); Yao Zhan, Zhejiang (CN); Bo Liu, Zhejiang (CN); Sikai Wang, Zhejiang (CN)

(73) Assignee: ZHEJIANG ORIENT GENE BIOTECH CO., LTD, Zhejiang (CN)

( * ) Notice: Subject to any disclaimer, the term of this patent is extended or adjusted under 35 U.S.C. 154(b) by 466 days.

(21) Appl. No.: 17/892,732

(22) Filed: Aug. 22, 2022

(65) Prior Publication Data
US 2024/0020940 A1    Jan. 18, 2024

(30) Foreign Application Priority Data
Jul. 18, 2022    (CN) .......................... 202210854796.1

(51) Int. Cl.
*G06V 10/22*    (2022.01)
*G06V 10/44*    (2022.01)
(Continued)

(52) U.S. Cl.
CPC ............ *G06V 10/225* (2022.01); *G06V 10/44* (2022.01); *G06V 10/50* (2022.01); *G06V 10/82* (2022.01); *G06V 30/10* (2022.01); *G16H 10/60* (2018.01)

(58) Field of Classification Search
CPC ...... G06V 10/225; G06V 30/10; G06V 10/82; G06V 10/50; G06V 10/44; G16H 10/60
See application file for complete search history.

(56) References Cited

U.S. PATENT DOCUMENTS

| | | | |
|---|---|---|---|
| 4,857,453 | A | 8/1989 | Ullman et al. |
| 5,073,484 | A | 12/1991 | Swanson et al. |

(Continued)

FOREIGN PATENT DOCUMENTS

| | | |
|---|---|---|
| AU | 2004226798 A1 | 10/2004 |
| CN | 101103931 B | 9/2011 |
| JP | 4579902 B2 | 11/2010 |

*Primary Examiner* — David Bilodeau
(74) *Attorney, Agent, or Firm* — MUNCY, GEISSLER, OLDS & LOWE, P.C.

(57) ABSTRACT

An automatic identification method, apparatus and device for detection results of an immunoreagent card. The method includes identifying a detection character and an identification code on a detection image of an obtained immunoreagent card; forming a corresponding target area based on the detection character, determining a central sub-area in the target area and calculating histogram information of the central sub-area; detecting a non-uniform area in the target area when the histogram information is between minimum and maximum grayscale statistical thresholds, and conducting brightness equalization processing on the non-uniform area; calculating the histogram information of the target area after equalization processing and determining a chromaticity of the target area based on a grayscale statistical threshold; forming an immune result of automatic identification according to the chromaticity; and binding the identified immune result with a serial number corresponding to the identification code, and returning the identified immune result to a user.

20 Claims, 6 Drawing Sheets

(51) Int. Cl.
*G06V 10/50* (2022.01)
*G06V 10/82* (2022.01)
*G06V 30/10* (2022.01)
*G16H 10/60* (2018.01)

(56) References Cited

U.S. PATENT DOCUMENTS

| | | | |
|---|---|---|---|
| 5,119,831 A | 6/1992 | Robin et al. | |
| 5,185,127 A | 2/1993 | Vonk | |
| 5,275,785 A | 1/1994 | May et al. | |
| 5,416,000 A | 5/1995 | Allen et al. | |
| 5,504,013 A | 4/1996 | Senior | |
| 5,602,040 A | 2/1997 | May et al. | |
| 5,622,871 A | 4/1997 | May et al. | |
| 5,654,162 A | 8/1997 | Guire et al. | |
| 5,656,503 A | 8/1997 | Candee | |
| 5,686,315 A | 11/1997 | Pronovost et al. | |
| 5,766,961 A | 6/1998 | Pawlak et al. | |
| 5,770,460 A | 6/1998 | Pawlak et al. | |
| 5,916,815 A | 6/1999 | Lappe | |
| 5,976,895 A | 11/1999 | Cipkowski | |
| 6,140,136 A | 10/2000 | Lee | |
| 6,187,269 B1 | 2/2001 | Lancesseur et al. | |
| 6,187,598 B1 | 2/2001 | May et al. | |
| 6,228,660 B1 | 5/2001 | May et al. | |
| 6,235,241 B1 | 5/2001 | Catt et al. | |
| 6,248,598 B1 | 6/2001 | Bogema | |
| 6,306,642 B1 | 10/2001 | Nelson et al. | |
| 6,352,862 B1 | 3/2002 | Davis | |
| 6,372,515 B1 | 4/2002 | Casterlin et al. | |
| 6,379,620 B1 | 4/2002 | Tydings et al. | |
| 6,403,383 B1 | 6/2002 | Casterlin et al. | |
| 8,114,027 B2 | 2/2012 | Triva | |
| 8,317,728 B2 | 11/2012 | Quick et al. | |
| 8,979,784 B2 | 3/2015 | Triva | |
| 9,011,358 B2 | 4/2015 | Triva | |
| 9,173,779 B2 | 11/2015 | Triva | |
| 10,327,741 B2 | 6/2019 | Triva | |
| 2004/0227758 A1* | 11/2004 | Curry | G06T 7/194 345/426 |
| 2009/0208055 A1* | 8/2009 | Chin | G06V 10/25 382/103 |
| 2016/0014316 A1* | 1/2016 | Liao | G06V 10/141 348/223.1 |
| 2021/0172945 A1* | 6/2021 | Armbruster | G01N 21/8483 |
| 2021/0343404 A1* | 11/2021 | Hunt | G16H 10/60 |
| 2023/0177680 A1* | 6/2023 | Adsul | G06T 7/0012 348/222.1 |

\* cited by examiner

AUTOMATIC IDENTIFICATION METHOD, APPARATUS AND DEVICE FOR DETECTION RESULTS OF IMMUNOREAGENT CARD

TECHNICAL FIELD

The present invention relates to the field of detection, and in particular, to an automatic identification method, apparatus and device for detection results of an immunoreagent card.

BACKGROUND

The continuous global spread of the novel coronavirus pandemic has seriously affected people's normal life and social and economic development. To curb its spread, it is necessary to continuously observe the results of pathogen detection in the public. Centralized immunization (antigen) detection is greatly difficult, not only does it need to mobilize a lot of manpower and material resources and does it have a wide range of influence, but also centralized detection has the risk of mutual infection.

In order to solve the problems existing in centralized immunodetection, personal detection reagent cards have been developed currently. Users can use immune reagent cards for testing by themselves, such as home testing. After testing, the staff will recover the reagent cards and confirm detection results. Although this detection manner solves the problem of people gathering, the recovery and confirmation of the reagent cards still require a large workload, and the consumption of manpower and material resources is still very large.

In addition, the detection results of the immune reagent cards are currently confirmed by the staff's eye observation. When the virus content carried by a patient is relatively low, a detection result will show a weak positive with very low color rendering. It is difficult to accurately distinguish weak positives and negatives by human observation, and misjudgment is very likely to occur. In addition, self-testing of infected families has gradually become popular, but when test results are read by naked eyes, a person tested is not a professional, and when a weak line appears in a detection area, it is difficult for an operator to distinguish whether it is truly positive or falsely positive, which causes great uncertainty.

Therefore, it is necessary to improve current methods for reading results, so as to increase the convenience of the operator and simultaneously enable to ensure the accuracy of reading.

SUMMARY

In order to overcome the deficiencies in the prior art, the present invention provides an automatic identification method, apparatus and device for detection results of an immunoreagent card.

In order to achieve the above purpose, the present invention provides an automatic identification method for detection results of an immunoreagent card, including:
identifying a detection character and an identification code on a detection image of an obtained immunoreagent card;
forming a corresponding target area based on the detection character, determining a central sub-area in the target area and calculating histogram information of the central sub-area;
detecting a non-uniform area in the target area when the histogram information of the central sub-area is between a minimum grayscale statistical threshold and a maximum grayscale statistical threshold, scanning the non-uniform area line by line, and conducting brightness equalization processing on a pixel value of each pixel point on a scanning line based on a brightness equalization coefficient;
identifying an edge of a detection line of the target area after equalization processing, and calculating the histogram information;
determining a chromaticity of the target area through an approximate linear relationship based on a grayscale statistical threshold and the calculated histogram information, and forming an immune result of automatic identification of the immunoreagent card according to the chromaticity of the target area corresponding to the detection character; and
binding the identified immune result with a serial number corresponding to the identification code of the immunoreagent card, and returning the identified immune result bound with the serial number to a user when receiving a user's query request based on the serial number.

In some implementations, the target area includes a detection area corresponding to a character T and a control area for detection results corresponding to a character C. The detection area can display lines of different chromaticities according to the quantity of an analyte in a sample. The control area for the detection results corresponding to the character C has a color display regardless of whether the detection area has a color display. If the control area does not have a color display, it means that an identified result is invalid.

In some implementations, the identified immune result is an immune test result of the analyte in the sample. In some implementations, the identified immune result is an antigen detection result.

According to an embodiment of the present invention, the step of determining the central sub-area in the target area and calculating the histogram information of the central sub-area includes:
dividing the target area into the central sub-area and a plurality of side sub-areas located on two sides of the central sub-area, and adaptively adjusting a range of the central sub-area based on a detection boundary of a non-uniform area of a historical immunoreagent card, the range of the central sub-area being greater than a sum of areas of all the side sub-areas;
identifying an edge of a detection line of the central sub-area to obtain a histogram of the central sub-area; and
conducting statistics on the histogram to obtain the histogram information.

According to an embodiment of the present invention, the automatic identification method for the detection results of the immunoreagent card further includes:
based on nucleic acid detection results fed back by the user, obtaining immunoreagent cards whose nucleic acid detection results are inconsistent with the identified immune result to form a first sample set; obtaining immunoreagent cards whose target area's chromaticity is near the grayscale statistical threshold and whose nucleic acid detection results are consistent with the identified immune result to form a second sample set;
dividing the first sample set and the second sample set into a non-uniform sample set and a uniform sample set separately according to immunoreagent card identification codes and equalization identification formed in a detection process of the non-uniform area;

optimizing the grayscale statistical threshold based on the uniform sample set of the first sample set and the uniform sample set of the second sample set; and optimizing the brightness equalization coefficient according to the optimized grayscale statistical threshold, the non-uniform sample set of the first sample set, the non-uniform sample set of the second sample set and a grayscale dispersion parameter of the target area after equalization processing.

This is because when the antigen detection result is positive, a person tested generally needs to undergo a nucleic acid test to further confirm whether antigen detection is correct. When the person is infected with a virus, antigen detection is only preliminary screening. When detection is positive, confirmation detection for a viral nucleic acid is generally required. Nucleic acid detection is confirmation detection, and the detection sensitivity thereof is higher than that of antigen detection. Therefore, when the antigen detection result is judged positive by the automatic identification method of the present invention, further nucleic acid detection is required for confirmation. At this time, there may be inconsistency between a nucleic acid detection result and the antigen detection result. Therefore, an antigen detection result identification system of the present invention is further optimized by a system, especially a numerical value of a threshold is optimized.

The nucleic acid detection result here may be actively input from the system by the person tested, or extracted from a public database. Generally, the antigen detection result of the present invention is automatically uploaded to a database, i.e., a public epidemic prevention system. When an operator undergoes nucleic acid detection, his nucleic acid detection result is also input into the public epidemic prevention system. Therefore, the nucleic acid detection result can be extracted from the public epidemic prevention system, so as to realize calibration or optimization of immune results identified by an automatic identification apparatus for antigen detection. Preferably, nucleic acid detection results within 24 hours are generally selected to optimize a grayscale statistical threshold for antigen detection identification to ensure timeliness of data.

According to an embodiment of the present invention, non-uniform area detection and brightness equalization are conducted in the target area by a convolutional neural network, and the non-uniform samples of the first sample set and the second sample set are expanded into a training sample set of the convolutional neural network.

According to an embodiment of the present invention, coordinates of a plurality of characteristic positions are determined on the detection character and the identification code separately after the detection character and the identification code are identified, and an image area where the immunoreagent card is located is transformed into a same scale by affine transformation based on the coordinates of the plurality of characteristic positions; and a preset pixel window is extended based on each detection character to form the target area corresponding to the detection character.

According to an embodiment of the present invention, after an identification code representing an identity of a current immunoreagent card is identified, whether the current immunoreagent card is repeatedly uploaded is judged based on the serial number corresponding to the identification code; if the current immunoreagent card is repeatedly uploaded, then whether a last identification result of the immunoreagent card is abnormal is judged; if the last identification result is abnormal, the immunoreagent card is re-identified and a result of re-identification is bound to the serial number corresponding to the identification code.

According to an embodiment of the present invention, the automatic identification method for the detection results of the immunoreagent card further includes:

receiving a detection image of an immunoreagent reagent card photographed and uploaded by a user, and storing the detection image in a database server after the detection image is bound with an immunoreagent card serial number;

sending a plurality of detection image information to a plurality of identification nodes in a manner of intranet in-turn distribution by a queue form, the detection image information including the immunoreagent card serial number corresponding to the detection image of the immunoreagent card; and querying the database server by the identification nodes based on a received immunoreagent card serial number to obtain the detection image corresponding to the immunoreagent card serial number, identifying the detection image to obtain an identification result of the immunoreagent card, and binding the identification result with the current immunoreagent card serial number.

According to an embodiment of the present invention, the plurality of identification nodes are paralleled, and a plurality of parallel computing nodes are dynamically expanded under each of the plurality of identification nodes, and each of the identification nodes distributes the detection image information to the plurality of computing nodes under there in a manner of in-turn distribution.

According to an embodiment of the present invention, the detection character includes a character T or a character C.

According to an embodiment of the present invention, a target area corresponding to the character T is a detection area, and a target area corresponding to the character C is a control area for detection results.

According to an embodiment of the present invention, the target area corresponding to the character T is in a form of a line.

According to an embodiment of the present invention, the identified immune result is obtained based on the target area corresponding to the character T.

On the other hand, the present invention further provides an automatic identification apparatus for detection results of an immunoreagent card, including an obtaining and identification module, an area determination module, an equalization module, a calculating module, a result identification module and a returning module. The obtaining and identification module identifies a detection character and an identification code on a detection image of an obtained immunoreagent card. The area determination module forms a corresponding target area based on the detection character, determines a central sub-area in the target area and calculates histogram information of the central sub-area. The equalization module detects a non-uniform area in the target area when the histogram information of the central sub-area is between a minimum grayscale statistical threshold and a maximum grayscale statistical threshold, scans the non-uniform area line by line, and conducts brightness equalization processing on a pixel value of each pixel point on a scanning line based on a brightness equalization coefficient. The calculating module identifies an edge of a detection line of the target area after equalization processing, and calculates the histogram information. The result identification module determines a chromaticity of the target area through an approximate linear relationship based on a grayscale statistical threshold and the calculated histogram information, and forms an immune result of automatic identification of the immunoreagent card according to the chromaticity of the target area corresponding to each detection character. The returning module binds the identified immune result with a serial number corresponding to the identification code of the immunoreagent card, and returns the identified immune result bound with the serial number to a user when receiving a user's query request based on the serial number.

According to an embodiment of the present invention, the detection character is a character T, and a target area corresponding to the character T is a detection area.

According to an embodiment of the present invention, the detection area is in a form of a line.

On the other hand, the present invention further provides an electronic device, including one or more processors and a storage device. The storage device is used for storing one or more programs. When the one or more programs are executed by the one or more processors, the one or more processors are caused to implement the automatic identification method for the detection results of the immunoreagent card above.

To sum up, in the automatic identification method, apparatus and device for the detection results of the immunoreagent card provided by the present invention, judgment of negatives and strongly positives can be quickly and accurately realized based on the histogram information of the central sub-area, thereby greatly improving an identification rate. For the histogram information of the central sub-area between the minimum grayscale statistical threshold and the maximum grayscale statistical threshold (weakly positive or negative immunoreagent cards), brightness equalization is conducted on the target region to compensate for interference with the histogram information by an uneven brightness caused by photographing by the user, so that an identification accuracy rate can be greatly improved, and dual-index requirements of large-scale antigen detection in terms of identification accuracy rate and identification speed can be well met.

In addition, both the optimization of the range of the central sub-area based on the detection boundary of the non-uniform area and the optimization of the grayscale statistical threshold and the brightness equalization coefficient based on the multi-type sample sets expanded by nucleic acid detection results can further improve the accuracy rate and speed of identification.

In order to make the above and other purposes, features and advantages of the present invention more obvious and easy to understand, the preferred embodiments are hereinafter given specially and describe them in detail in combination with accompanying drawings.

DETAILED DESCRIPTION

Detection

Detection means assaying or testing for the presence or the absence of a substance or material such as, but not limited to, chemicals, organic compounds, inorganic compounds, metabolites, drugs or drug metabolites, organic tissue or metabolites thereof, antigens, proteins or polymers. Moreover, detection means testing the quantity of a substance or material. Further, assay also means immunodetection, chemical detection, enzymatic detection, and the like. A reagent card here is used for testing generally by an immunization method, and the so-called immunization method is carried out based on a manner of combination of antibodies and antigens. An immune test method here is generally to detect antigens or small chemical molecules in a sample, while a nucleic acid detection method is generally to detect the copy number of nucleic acids.

For example, when a virus is detected, the immunization method can be used for detecting the antigens, and the nucleic acid method is used for detecting the copy number of the virus. Generally, the sensitivity of nucleic acid detection is higher than that of antigen detection.

Samples

Samples that can be detected by the detection device of the present invention, or samples or specimens that can be collected by a collector include biological liquids (e.g. case liquids or clinical samples). Liquid samples or fluid specimens may be derived from solid or semi-solid samples, including excreta, biological tissues and food samples. Solid or semi-solid samples can be transformed into liquid samples by any proper method, such as mixing, mashing, macerating, incubating, dissolving or digesting solid samples with enzymolysis in a suitable solution (e.g., water, a phosphate solution or other buffer solutions). "Biological samples" include samples from animals, plants and food, for example, including urine, saliva, blood and components thereof, spinal fluid, vaginal secretion, semen, faeces, sweat, secreta, tissues, organs, tumors, cultures for tissues and organs, cell cultures and media from human or animals. A preferred biological sample is urine, preferably, biological samples are saliva, sputum, nasal secretion, and the like. Food samples include substances processed from food, final products, meat, cheese, wine, milk and drinking water. Plant samples are derived from any plants, plant tissues, plant cell cultures and media. "Environmental samples" are derived from the environment (for example, liquid samples, wastewater samples, soil texture samples, underground water, seawater and effluent samples from lakes and other water bodies). Environmental samples may further include sewage or other waste water.

Any analyte can be detected by using the appropriate immune detection element or immune testing element of the present invention. Preferably, the present invention is used for detecting small drug molecules in saliva and urine. Preferably, viruses, bacteria and other small molecular substances in saliva, throat or nasal cavity fluids can be detected. Any form of samples above, either initially solid or liquid, can be collected by the collector, as long as these liquids or liquid samples can be absorbed by an absorbing element; and the absorbing element is generally located on the collector. The absorbing element here is generally prepared from a water absorbent material and is initially dry. It can absorb liquid or fluid samples by capillary or other characteristics of the material of the absorbing element, so as to keep the fluid samples in the absorbing element. The absorbent material may be any liquid absorbing material such as sponge, filter paper, polyester fiber, gel, non-woven fabric, cotton, polyester film, yarn, flocking, etc. When a flocking swab is used, the flocking swab described in the following patents may be used for collecting the fluid samples as a part of the present invention: U.S. Pat. Nos. 8,114,027, 8,317,728, 8,979,784, 9,011,358, 9,173,779, 10,327,741, AU2004226798, JP4579902 and ZL200610099310.9. In some implementations, the absorbing element is hard when it is dry, for example, a sponge becomes soft when it is wet, and can be compressed after it becomes soft to release liquids. Of course, when it is a relatively sparse sponge, for example, a sponge swab, liquid samples can be still absorbed in a little amount, for example, 5 to 100 microliters; for example, a sponge swab described in a U.S. Provisional Application 63/300,811 with application number: Jan. 19, 2022 may be also used in the present invention as a specific embodiment of the collector.

Of course, the absorbing element is not necessarily prepared by a water absorbent material but may be prepared by a non-water-absorbent material. However, the absorbing element has pores, threads, and cavities, and samples may be collected on these structures. These samples are generally solid or semi-solid samples, and are filled between threads, or in cavities or pores to be collected. Of course, optionally, the absorbing element may consist of some non-water-absorbent fibers and hairs; these materials are used for scratching solid, semi-solid or liquid samples such that these samples are maintained on the absorbing element.

Downstream and Upstream

Figure 9:
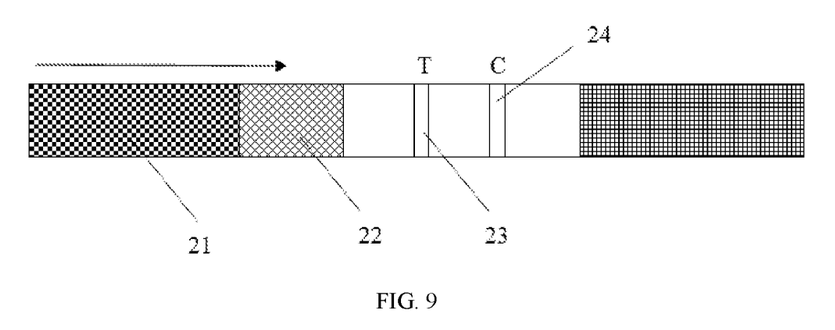
FIG. 9 shows a schematic structural diagram of a detection reagent in an immunoreagent card in FIG. 4.

Downstream or upstream is divided according to a flow direction of a liquid, generally, a liquid or fluid flows to a downstream area from an upstream area. The downstream area receives the liquid from the upstream area, and the liquid also may flow to the downstream area along the upstream area. Here the areas are generally divided according to the flow direction of the liquid. For example, on some materials that use capillary force to promote the liquid to flow, the liquid can overcome gravity to flow against the gravity direction, at this time, the upstream and downstream areas are still divided according to the flow direction of the liquid. For example, as shown in FIG. 9, the testing element mentioned in the present invention has, from upstream to downstream, a sample application area 21 for sample application, a labeled area 22, a detection area 23, a control area 24 and an absorption area. The sample application area 21 is located upstream of the labeled area 22, and the detection area 23 is located downstream of the labeled area 22, the control area 24 is located downstream of the detection area 23, and the absorption area is located downstream of the control area 24. Generally, a fluid flows to the downstream from the upstream along the flow direction of the testing element. In an implementation of the present invention, when a reagent card is vertical, a liquid sample will overcome gravity due to capillary force to flow from bottom to top, namely, flowing to the downstream from the upstream once it contacts the sample application area. In this way, the liquid sample flows through the labeled area 22, then to the detection area 23, then to the control area 24, and finally flows to the water absorbing area.

Gas Flow or Liquid Flow

Gas flow or liquid flow means that a liquid or gas can flow from one place to another place, and may pass through some physical structures to play a guiding role in a flow process. The "passing through some physical structures" generally means that the liquid passes through the surface of these physical structures or their internal spaces and flows to another place passively or actively, where passivity is usually caused by external forces, such as the flow under capillary action and air pressure action. The flow here may also be a flow due to self-action (gravity or pressure) of the liquid or gas, and also may be a passive flow. The fluid under the action of air pressure may flow in a forward direction, or flow in a reverse direction; or a fluid is urged to flow from one position to another position under the action of air pressure. Here, the flow does not mean that a liquid or a gas is necessarily present, but indicates a relationship or state between two objects under some circumstances. In case of presence of liquid, it can flow from one object to another. Here it means the state in which two objects are connected. In contrast, if there exists no liquid flow or gas flow state between the two objects, and a liquid exists in or above one object but cannot flow into or on another object, it is a non-flow, non-liquid or non-gas flow state.

Testing Element

Figure 4:
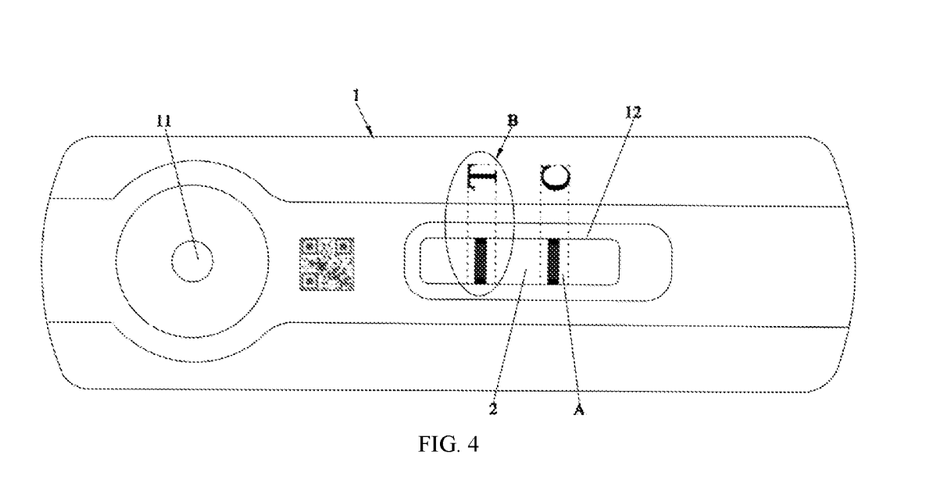
FIG. 4 shows a schematic structural diagram of determining a target area and a central area on an image area where an immunoreagent card is located.

In the present invention, for example, a reagent card as shown in FIG. 4, such a reagent card generally includes an outer housing and a testing element included in the housing. The housing includes a sample application hole 11 for dropwise adding a liquid sample, and a detection window for reading a test result. With respect to the testing element, the detection window for reading the test result corresponds to the detection area 23 and the control area 24 of the testing element, while sample application hole 11 for dropwise adding the liquid corresponds to the sample application area 21 of the testing element. The "immune testing element" here refers to an element that can be used for detecting whether a sample or a specimen contains an interested analyte. Such testing can be based on any technical principles, such as immunology, chemistry, electricity, optics, molecular science, antigens, physics, etc. The testing element can be a lateral flow test strip that can detect a variety of analytes. Of course, other suitable testing elements can also be used in the present invention.

In some implementations, the testing element or a testing card containing the testing element herein is based on an immunogen to detect the analyte in the sample.

Various testing elements can be combined for use in the present invention. One form of the testing elements is test paper or lateral flow test paper. The test papers used for analyzing the analyte (such as drugs or metabolites that show physical conditions) in the sample can be of various forms such as immunoassay or chemical analysis. The analysis mode of non-competitive method or competitive method can be adopted for test papers. A test paper generally contains a water absorbent material that has a sample application area, a reagent area and a detection area. Fluid or liquid samples are added to the sample application area and flow to the reagent area through capillary action. If an analyte exists in the reagent area, a sample will bind to a reagent. Then, the sample continues to flow to the detection area. Other reagents such as molecules that specifically bind to the analyte are fixed in the detection area. These reagents react with the analyte (if any) in the sample and bind to the analyte in this area, or bind to certain reagent in the reagent area. A marker used for displaying a detection signal exists in the reagent area or a detached labeled area.

The typical non-competitive method analysis mode: if a sample contains an analyte, a signal will be generated; and if not, no signal will be generated. The competitive method: if no analyte exists in the sample, a signal will be generated; and if an analyte exists, no signal will be generated.

The testing element may be a test paper, which can be water absorbent or non-absorbing materials. The test paper can contain several materials used for delivery of liquid samples. One material can cover the other material. For example, a filter paper covers a nitrocellulose membrane. One area of the test paper can be of one or more materials, and the other area uses one or more other different materials. The test paper can stick to a certain support or on a hard surface for improving the strength of holding the test paper.

The analyte is detected through a signal generating system. For example, one or more enzymes that specifically react with this analyte is or are used, and the above method of fixing the specifically bound substance on the test paper is used for fixing a combination of one or more signal generating systems in an analyte detection area of the test paper. The substance that generates a signal can be in the sample application area, the reagent area or the detection area, or on the whole test paper, and one or more materials of the test paper can be filled with this substance. A solution containing a signifier is added onto the surface of the test paper, or one or more materials of the test paper is or are immersed in a signifier-containing solution, and the test paper containing the signifier solution is made dry. The signifier here is generally displayed in a detection line or a structure control area, and has the depth of color or the intensity of chromaticity.

Each area of the test paper can be arranged in the following way: sample application area 21, reagent area 22, detection area 23, control area 24, area determining whether the sample is adulterated, and liquid sample absorbing area. The control area 24 is located behind the detection area 23. All areas can be arranged on a test paper that is only made of one material. Also, different areas may be made of different materials. Each area can directly contact the liquid sample, or different areas are arranged according to the flow direction of liquid sample; and a tail end of each area is connected and overlapped with a front end of the other area. Materials used can be those with good water absorption such as filter papers, glass fibers or nitrocellulose membranes. The test paper can also be in the other forms.

A nitrocellulose membrane test strip is commonly used, that is, a detection area includes a nitrocellulose membrane (NC) on which a specific binding molecule is fixed to display a detection result; and other test strips such as cellulose acetate membrane or nylon membrane test strips can also be used. For example, test strips and apparatuses with test strips are disclosed in the following patents: U.S. Pat. Nos. 4,857,453; 5,073,484; 5,119,831; 5,185,127; 5,275,785; 5,416,000; 5,504,013; 5,602,040; 5,622,871; 5,654,162; 5,656,503; 5,686,315; 5,766,961; 5,770,460; 5,916,815; 5,976,895; 6,248,598; 6,140,136; 6,187,269; 6,187,598; 6,228,660; 6,235,241; 6,306,642; 6,352,862; 6,372,515; 6,379,620, and 6,403,383. The test strips and similar apparatuses with test strips disclosed in the above patent literatures may be applied in the testing element or detection apparatus of the present invention for analyte detection, for example, the detection of an analyte in a sample.

The test strips used in the present invention may be those what we commonly called lateral flow test strip, whose specific structure and detection principle are well known by those with ordinary skill in the art. Common test paper (FIG. 9) includes a sample collecting area or a sample application area 21, a labeled area 22, a detection area 23, a control area 24 and a water absorbing area; the sample application area 21 includes a sample receiving pad, the labeled area includes a labeled pad, the water absorbing area may include a water absorbing pad; where the detection area includes necessary chemical substances for detecting the presence or absence of analyte, such as immunoreagents or enzyme chemical reagents. The nitrocellulose membrane test strip is commonly used, that is, the detection area 23 includes a nitrocellulose membrane on which specific binding molecule is fixed to display a detection result; and other test strips such as cellulose acetate membrane or nylon membrane test strips can also be used. Of course, in the downstream of the detection area, there may also be a detecting result control area 24. Generally, test strips appear on the control area 24 and the detection area 23 in the form of a horizontal line, that is a detection line or a control line. Such test strips are conventional. Of course, they can also be other types of test strips using capillary action for detection. In addition, there are often dry chemical reagent components on the test strips, for example, immobilized antibodies or other reagents. When the test strips meet a liquid, the liquid flows along the test strips with the capillary action, and the dry reagent components are dissolved in the liquid, then the liquid flows to the next area, the dry reagents are treated and reacted for necessary detection. The liquid flow mainly relies on the capillary action. Here, all of them can be applied to the detection device of the present invention or can be disposed in a detection chamber to contact with the liquid samples or used for detecting the presence or absence of an analyte in the liquid samples that enter the detection chamber, or the quantity thereof.

In addition to that the above test strips or the lateral flow test strips are used for being in contact with the liquid samples by themselves to test whether the liquid samples contain the analyte, the testing element of the present invention may be used as a detection device by itself to detect the analyte in the samples. Therefore, the detection device here is equal to a testing element. For example, after being mixed with a treatment solution, a fluid sample is detected with a testing element directly. As will be described in detail below, when the receiving device is described to treat a fluid sample, the testing element may be used for detection alone.

Analyte

Examples that can use the analyte related to this invention include some small molecular substances, including drugs (such as drugs of abuse). "Drugs of Abuse" (DOA) refers to using a drug (playing a role of paralyzing nerves usually) not directed to a medical purpose. Abuse of these drugs will lead to physical and mental damage, produce dependency, addiction and/or death. Examples of DOA include cocaine, amphetamine AMP (for example, Black Beauty, white amphetamine table, dextroamphetamine, dextroamphetamine tablet, and Beans); methylamphetamine MET (crank, methamphetamine, crystal, speed); barbiturate BAR (e.g., Valium, Roche Pharmaceuticals, Nutley, and New Jersey); sedative (namely, sleep adjuvants); lysergic acid diethylamide (LSD); depressor (downers, goofballs, barbs, blue devils, yellow jackets, methaqualone), tricyclic antidepressants (TCA, namely, imipramine, Amitryptyline and Doxepin); methylene dioxymetham-phetamine (MDMA); phencyclidine (PCP); tetrahydrocannabinol (THC, pot, dope, hash, weed, and the like). Opiates (namely, morphine MOP or, opium, cocaine COC; heroin, oxycodone hydrochloride); antianxietics and sedative hypnotics, antianxietics are drugs for alleviating anxiety, tension, fear, stabilizing emotion and having hypnosis and sedation, including benzodiazepines (BZO), non-typical BZs, fusion dinitrogen NB23Cs, benzoazepines, ligands of a BZ receptor, open-loop BZs, diphenylmethane derivatives, piperazine carboxylates, piperidine carboxylates, quinazoline ketones, thiazine and thiazole derivatives, other heterocyclic, imidazole sedatives/analgesics (e.g., oxycodone hydrochloride OXY, metadon MTD), propylene glycol derivatives, mephenesin carbamates, aliphatic compounds, anthracene derivatives, and the like. The detection device of the present invention may be also used for detecting drugs, which belong to medical use but is easy to be taken excessively, such as tricyclic antidepressants (Imipramine or analogues), acetaminophen and the like. These medicines will be metabolized into small molecular substances after being absorbed by the human body, and these small molecular substances will exist in blood, urine, saliva, sweat and other body fluids or in some of the body fluids.

For example, analytes detected with the present invention include, but are not limited to, creatinine, bilirubin, nitrite, proteins (non-specific), hormones (e.g., human chorionic gonadotropin, progesterone hormone, follicle stimulating hormone, etc.), blood, leukocytes, sugars, heavy metals or toxins, bacterial substances (such as proteins or carbohydrates against specific bacteria, e.g., *Escherichia coli* 0157: H7, *Staphylococcus, Salmonella, Clostridium, Campylobacter, L. monocytogenes, Vibrios*, or *Bacillus cereus*) and substances associated with physiological characteristics in urine samples, such as pH and proportion. The chemical analysis of any other clinical urine may be conducted by means of a lateral cross-flow detection way and in combination with the device of the present invention. In some implementations, a treatment solution contained in a receiving device contains no analyte.

DETAILED DESCRIPTION OF THE EMBODIMENTS

The following implementations are merely examples to illustrate how the present invention is implemented, these descriptions are not intended to further limit the present invention, and the protection scope of the present invention is defined by the claims.

Reagent card-based immunodetection alleviates the problem of personnel concentration. However, due to the low color of weak positives on reagent cards and large-scale detection, the number of reagent cards is very large; manual identification is not only prone to misjudgment of weak positives, but also has a huge workload and a low identification speed, which greatly limits the application of reagent cards in large-scale antigens. In view of this, the present embodiment provides an automatic identification method, apparatus and device for detection results of an immunoreagent card with a high automatic identification accuracy rate and a high speed.

In short, it is to take pictures of results of a detection area and a control area in a detection window in a manner of taking pictures, and then use internal operation to automatically identify test results. The "taking pictures" here can be conducted by using the photographing function of current mobile phones or tablet computers; the test results are mainly results tested by an immunization method.

Figure 1:
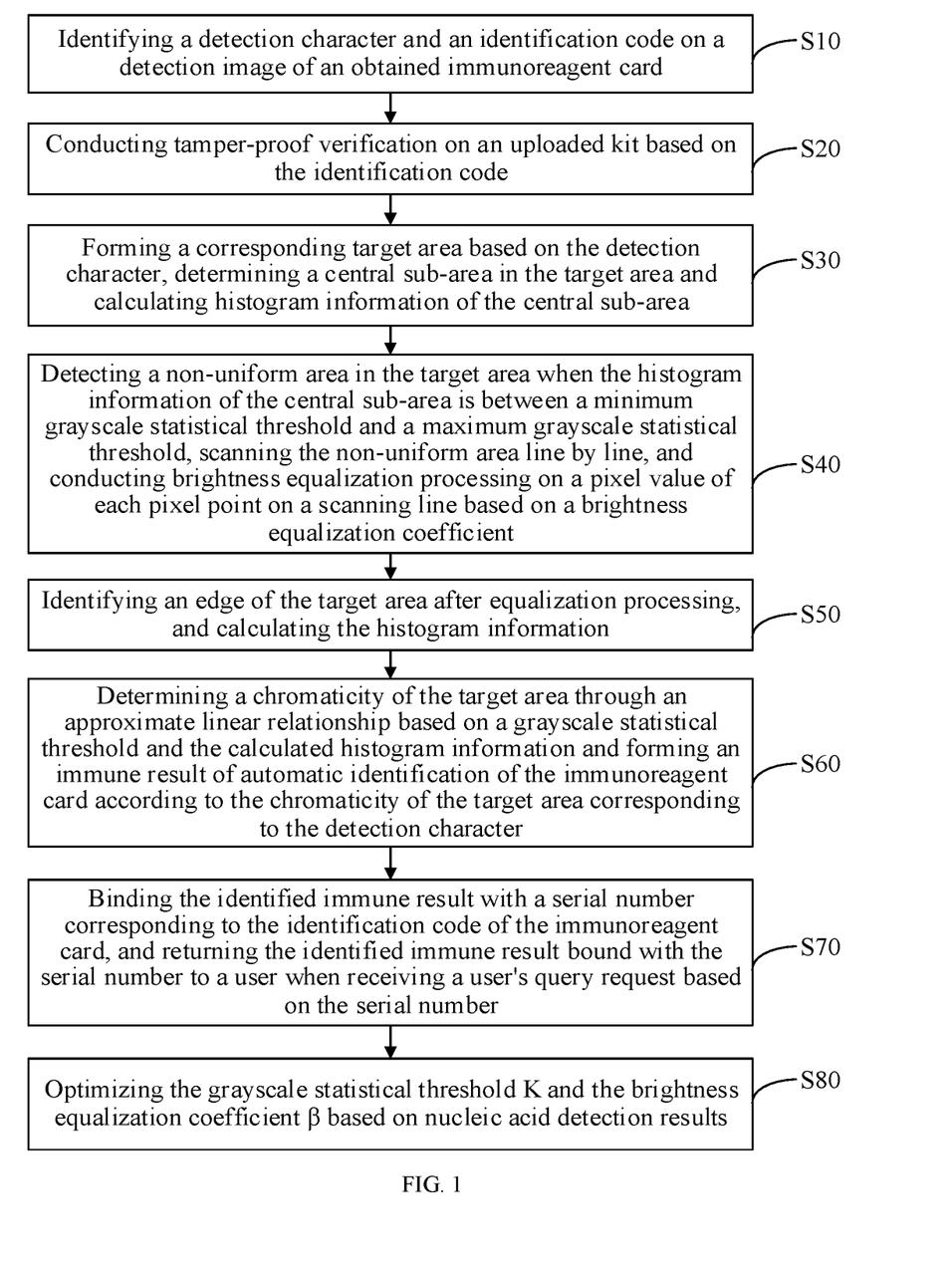
FIG. 1 shows an identification flowchart of an automatic identification method for detection results of an immunoreagent card provided by an embodiment of the present invention.

As shown in FIG. 1, an automatic identification method for detection results of an immunoreagent card provided by the present embodiment includes: identifying a detection character and an identification code on a detection image of an obtained immunoreagent card (Step S10); forming a corresponding target area based on the detection character, determining a central sub-area in the target area and calculating histogram information of the central sub-area (Step S30); detecting a non-uniform area in the target area when the histogram information of the central sub-area is between a minimum grayscale statistical threshold and a maximum grayscale statistical threshold, scanning the non-uniform area line by line, and conducting brightness equalization processing on a pixel value of each pixel point on a scanning line based on a brightness equalization coefficient (Step S40); identifying an edge of a detection line of the target area after equalization processing, and calculating the histogram information (Step S50); determining a chromaticity of the target area through an approximate linear relationship based on a grayscale statistical threshold and the calculated histogram information and forming an immune result of automatic identification of the immunoreagent card according to the chromaticity of the target area corresponding to each detection character (Step S60); and binding the identified immune result of the immunoreagent card with a serial number corresponding to the identification code of the immunoreagent card, and returning the identified immune result bound with the serial number to a user when receiving a user's query request based on the serial number (Step S70).

The automatic identification method for the detection results of the immunoreagent card provided by the present embodiment will be described in detail below in combination with FIG. 1 to FIG. 9.

Preparation of the Immunoreagent Card:

The reagent card for detection of novel coronavirus by an immunization method prepared by the present embodiment is shown in FIG. 4 and FIG. 9, including a test paper (FIG. 9) and a housing containing the test paper (FIG. 4). According to the direction of liquid flow, from upstream to downstream, the test paper is sequentially distributed with a sample application area 21, a labeled area 22, a detection area 23, a control area 24 and a water absorbing area. A sample application hole 11 on the housing 1 is located on the sample application area 21. The detection area 23 and the control area 24 are exposed by a window 12 on the housing 1. The water absorbing area is prepared by using a general water absorbing filter paper as a water absorbing pad. The sample application area 21 uses a sample application pad whose material is glass fiber, so that a sample added through the sample application hole 11 flows onto the glass fiber, which is then mixed with the sample to flow onto a labeled pad; the labeled area 22 is made into the labeled pad, including labeling particles (such as gold particles, latex particles or dyes, or other colored labeling substances) conjugated antigens or antibodies, then a labeling mixture is sprayed on a polyester film through spraying equipment to make the labeled pad, and a labeling substance on the labeling pad can flow with flow of a liquid; the detection area 23 and the control area 24 use a nitrocellulose membrane, antibodies or antigens on a detection line are dissolved with a buffer solution PBS, and then dot-membrane equipment is used for drawing a line on the nitrocellulose membrane, so as to make a distance between different antibodies be 3 to 8 millimeters, and then the nitrocellulose membrane is put in an oven to be dried for standby use, the antibodies, antigens or other binding substances processed on the membrane are generally immobile.

After preparation of the water absorbing area, the sample application area, the labeled area, the detection area and the control area are respectively completed, they are assembled so that one end of the sample application pad is superimposed on one end of the labeled pad, the other end of the labeled pad is superimposed on the nitrocellulose membrane, and the nitrocellulose membrane at one end of a control line is superimposed by the water absorbing filter paper, in this way, a whole test strip is formed and then assembled in the housing of the reagent card (FIG. 4). The sample application hole 11 on the housing of the reagent card corresponds to the sample application pad, and the nitrocellulose membrane corresponds to the detection window 12 on the housing. The housing of the reagent card has words of a detection character T or C, an area corresponding to the character T is the detection area, and positive or negative results are judged by reading a chromaticity of the detection area. When a colored line appears in the detection area, it is generally positive, and when there is no color, it is negative. At this time, there is always color in the control area corresponding to the character C. If the control area corresponding to the character C has no color, it means that a detection result is invalid.

In the automatic identification method for the detection results of the immunoreagent card provided by the present embodiment, the detection image of the immunoreagent card in Step S10 is uploaded by an application program in an intelligent terminal after being self-detected and photographed by the user. The intelligent terminal may be a mobile phone or a tablet computer, and the application program may be third-party application programs such as WeChat Mini Programs, Alipay Mini Programs, or Mini Program of the General Office of the People's Government of Zhejiang Province.

Step S10 is performed after the detection image of the immunoreagent card uploaded by the user is obtained. The step includes: performing binarization processing on the detection image of the immunoreagent card, and determining a position of the immunoreagent card in the detection image. The detection character and the identification code on the immunoreagent card are identified through an OCR character. In the present embodiment, the detection character includes a character T and/or a character C, preferably the character T. The identification code represents an identity of the immunoreagent card, and each identification corresponds to one immunoreagent card serial number, the identification code being a two-dimensional code. However, the present invention does not make any limitation to this. In other embodiments, the identification code can also be a bar code.

Figure 2:
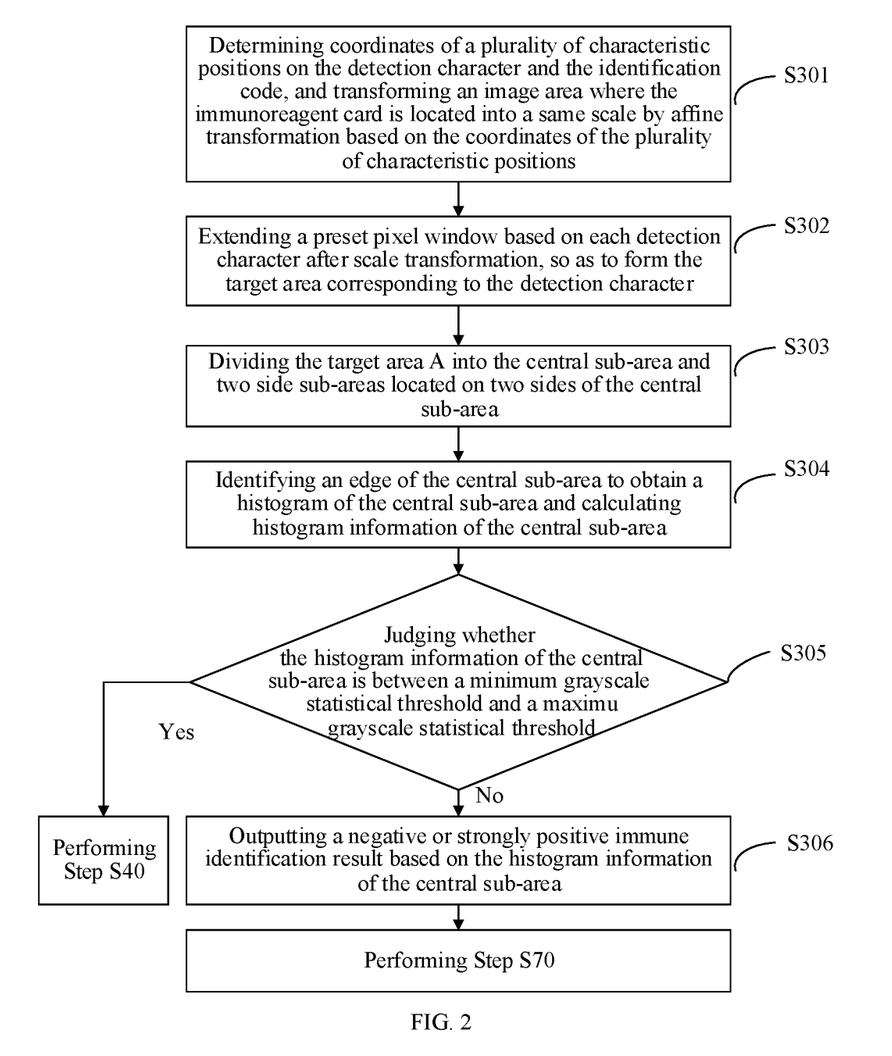
FIG. 2 shows a schematic specific flow diagram of Step S30 in FIG. 1.

Step S30 is performed after the detection character T and/or the character C are/is identified, i.e., determining the target area corresponding to each detection character, and calculating the histogram information by per-pixel statistics in the target area. The per-pixel statistics can accurately count a grayscale value of each pixel point in the target area so as to improve the accuracy of identification, and the determination of the target area greatly reduces a calculation range and realizes fast and accurate identification of the detection line.

Figure 5:
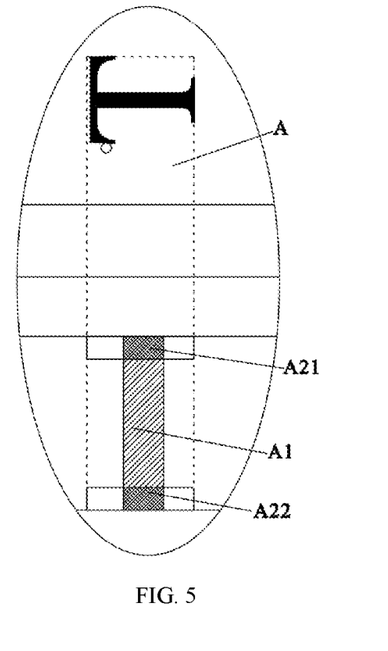
FIG. 5 shows an enlarged schematic diagram of B in FIG. 4.

The step includes: Step S301, determining coordinates of a plurality of characteristic positions on the detection character and the identification code, and transforming an image area where the immunoreagent card is located into a same scale by affine transformation based on the coordinates of the plurality of characteristic positions. Different users have different photographing angles and photographed images also have different sizes. To realize the determination of the target area, in the present embodiment, the image area where the immunoreagent card is located is subjected to unified scale transformation by affine transformation. As shown in FIG. 4 and FIG. 5, the plurality of characteristic positions are a lower edge midpoint of the detection character C (such as a circle point position of the lower edge of the character C in FIG. a lower edge midpoint of the detection character T and four angular points of any two rectangles on the two-dimensional code. The following affine transformation equation is solved based on coordinate pairs of the six characteristic positions so as to conduct scale transformation.

$$\begin{bmatrix} s\cos(\theta) & -s\sin(\theta) & t_x \\ s\sin(\theta) & s\cos(\theta) & t_y \\ 0 & 0 & 1 \end{bmatrix} \begin{bmatrix} x \\ y \\ 1 \end{bmatrix} = \begin{bmatrix} x' \\ y' \\ 1 \end{bmatrix}$$

Where s is a scale transformation factor, and (x', y') is a transformation position of a point (x, y) in the image area where the immunoreagent card is located.

Step S302, extending a preset pixel window based on the detection character after scale transformation, so as to form the target area corresponding to the detection character; that is, the characters T and C correspond to a target area A separately. The preset pixel window is a rectangular window, and two long sides of the rectangular window are tangent lines where two boundary points of the corresponding character are located; an upper short side of the rectangular window is an upper edge point of the corresponding detection character, and a lower short side thereof extends to a lower edge of the test paper 2 in the detection window 12. However, the present invention does not make any limitation to this. Other preset pixel window shapes including the detection area on the test paper are all within the protection scope of the present invention.

Since the test paper 2 is embedded in the detection window 12 on the housing 1 of the immunoreagent card, and affected by the photographing angle of the user, a light source and the projection of the edge of the detection window of the immunoreagent card, shadows or highlighted areas are likely to appear on the test paper 2, resulting in uneven brightness in the target area, especially in an area near the edge of the detection window 12 of the immunoreagent card; while the highlighted or shadowed areas will seriously affect the edge identification of the detection line. Therefore, the present embodiment provides to perform per-pixel brightness equalization processing on areas with uneven brightness to improve the effect of edge identification. However, for large-scale antigen detection, the per-pixel brightness equalization processing not only reduces an identification rate, but also has very high requirements for the performance of computer equipment.

By analyzing a large number of detection images of immunoreagent cards, it is found that moderately positive and strongly positive detection lines have relatively strong chromaticity as a whole; while for a large number of negatives, the central chromaticity of the detection area is close to zero. In view of this, in the automatic identification method for the detection results of the immunoreagent card provided by the present embodiment, in Step S30, it is proposed to determine the central sub-area A1 in the target area A, and to quickly identify negatives and moderate and strong positives based on the histogram information in the central sub-area A1. Specifically, Step S20 further includes:

Step S303, dividing the target area A into the central sub-area A1 and two side sub-areas A21 and A22 located on two sides of the central sub-area. Adaptively adjusting a range of the central sub-area A1 based on a detection boundary of a non-uniform area of a historical immunoreagent card (Step S401), the range of the central sub-area A1 being greater than a sum of areas of all the side sub-areas.

Step S304, identifying an edge of a detection line of the central sub-area A1 to obtain a histogram of the central sub-area, and calculating histogram information of the central sub-area A1.

Step S305, judging whether the histogram information of the central sub-area A1 is between a minimum grayscale statistical threshold and a maximum grayscale statistical threshold. If yes, continuing to perform Step S40; if not, performing Step S306, i.e., outputting a negative or moderately and strongly positive immune identification result based on the histogram information of the central sub-area A1. Then performing Step S70. It is judged that a detection image of a current immunoreagent card is negative when the histogram information of the central sub-area A1 is less than the minimum grayscale statistical threshold; if the histogram information of the central sub-area A1 is greater than the maximum grayscale statistical threshold, It is judged that the detection image of the current immunoreagent card is positive.

Through a large number of sample tests, it is obtained that the identification accuracy rate of negatives and moderate and strong positives based on the central sub-area A1 can reach more than 90%. In terms of the identification rate, the central sub-area A1 is less affected by uneven illumination and the grayscale gradient of the boundary of the moderately and strongly positive detection line changes greatly, so the edge identification speed of the detection line is very high, so that the identification speed can be greatly improved and rapid identification of negative images and moderately and strongly positive images can be realized.

In the process of identifying immune results based on the detection image of the immunoreagent card, the color rendering of a weakly positive detection line is very low, and the uneven illumination will seriously affect the accuracy rate of identification. Therefore, Step S40 is performed for the detection image of the immunoreagent card in which the histogram information of the central sub-area A1 is between the minimum grayscale statistical threshold and the maximum grayscale statistical threshold, a non-uniform area is detected in the target area, the non-uniform area is scanned line by line, and brightness equalization processing is conducted on a pixel value of each pixel point on a scanning line based on a brightness equalization coefficient.

Step S401, detecting the non-uniform area in the target area A. A grayscale value variance of each pixel point in a sliding window A (x, y) centered on the pixel point (x, y) is calculated; and whether an area where the sliding window is located is the non-uniform area is judged based on the grayscale value variance. Where the larger the grayscale value variance, the stronger the change of the grayscale value of pixels in the sliding window. Step S402, scanning the non-uniform area line-by-line and conducting brightness equalization processing on each pixel point on the scanning line based on the following formula.

$$I^*(x, y) = \frac{\overline{\sigma}}{\sigma + \alpha}(I(x, y) - \mu) + \beta$$

Where I (x, y) represents a pixel grayscale value at (x, y) in the non-uniform area, μ represents an average grayscale value of all pixels in the sliding window centered on (x, y); σ represents a variance of all the pixels in the window; $\overline{\sigma}$ is a variance of σ; α is a value to prevent σ from being zero, and is generally 0.1; I^*(x, y) is a pixel grayscale value at (x, y) after brightness equalization; β is a brightness equalization coefficient, ranges from 0 to 255 and meets the following constraints:

$$|\min(\alpha(I(x,y)-\mu)| \leq \beta \leq 255 - \max(\alpha(I(x,y)-\mu)$$

Performing Step S50 after brightness equalization processing is conducted on the non-uniform area, i.e., identifying the edge of the detection line of the target area after equalization processing, and calculating the histogram information. Determining a chromaticity of the target area through an approximate linear relationship based on a grayscale statistical threshold K and the calculated histogram information. Specifically, it is considered that no detection line is formed in the target area when the calculated histogram information is less than the grayscale statistical threshold K; it is considered that the detection line has been formed in the target area if the calculated histogram information is greater than or equal to the grayscale statistical threshold K.

Forming an immune result of automatic identification according to the chromaticity of the target area corresponding to each detection character (Step S60). For negatives, there is only a detection line in the target area corresponding to the character C, while no detection line is formed in the target area corresponding to the character T; for positives, detection lines are formed in areas corresponding to the character C and the character T. Therefore, based on Step S50, an identified immune result of a negative or positive immunoreagent card is output for the chromaticities of the target areas corresponding to the character C and the character T.

Finally, performing Step S70. Binding the identified immune result of the immunoreagent card with a serial number corresponding to the identification code of the immunoreagent card, and returning the identified immune result corresponding to the serial number to a user when the user sends a query request based on the serial number of the immunoreagent card through third-party applications such as WeChat Mini Programs and Alipay Mini Programs.

1000 immunoreagent card detection image samples are randomly selected to form a test sample set. The test sample set is input into an apparatus for operating the automatic identification method for the detection results of the immunoreagent card provided by the present embodiment for identification. Identification rates are counted, and accuracy rate verification is conducted in combination with nucleic acid detection results of each sample. Specific data are shown in the following table:

| Sample types | Number (pieces) | Identification accuracy rate | Identification rate |
|---|---|---|---|
| Negative samples identified based on a central area | 698 | 91% | 0.2 ms |
| Moderately and strongly positive samples identified based on the central area | 65 | 93% | 0.2 ms |

-continued

| Sample types | Number (pieces) | Identification accuracy rate | Identification rate |
|---|---|---|---|
| Weakly positive samples compensated based on brightness equalization | 104 | 81% | 0.7 ms |
| Negative samples compensated based on brightness equalization | 133 | 83% | 0.7 ms |
| Weakly positive samples based on deep learning | 104 | 62% | / |

Where 104 weakly positive samples based on deep learning are the same as 104 weakly positive samples compensated based on brightness equalization.

It can be directly obtained from this data table that the negative samples and moderately and strongly positive samples based on the central area have the high identification accuracy rate and the very high identification speed. The identification rates of the weakly positive samples and negative samples compensated based on brightness equalization are also as high as more than 80%, especially the identification accuracy rate of the weakly positive samples is significantly higher than that of the weakly positive samples based on deep learning. An identification method based on deep learning is an identification mode formed in an initial research and development stage, but because characteristic parameters of weak positives are relatively close to those of negatives, scores of more weak positives are very close to those of negatives after deep learning fitting, and they cannot be distinguished by a score threshold. Therefore, the identification effect is not ideal, and in the above table, it is used as an identification control group for the weakly positive samples compensated based on brightness equalization.

Figure 3:
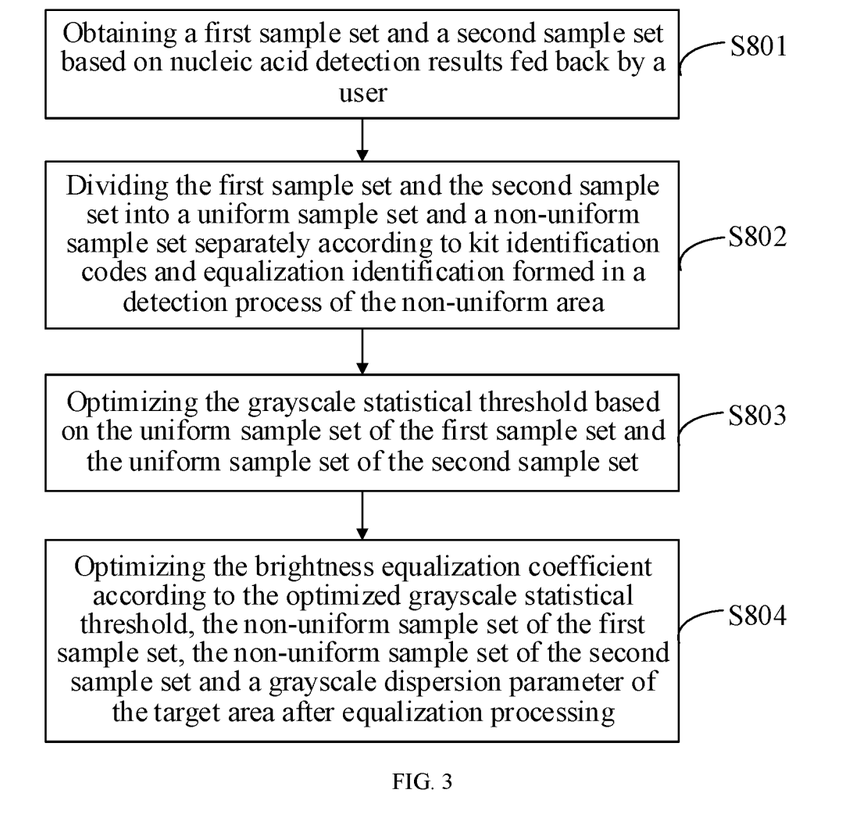
FIG. 3 shows a schematic specific flow diagram of Step S80 in FIG. 1.

The identification of negatives and moderately and strongly positives based on the central area A1 depends on the range of the central area A1. In this embodiment, the central area A1 will be gradually optimized according to the detection boundary of the non-uniform area in Step S401, thereby further improving the accuracy of identification. In addition, in order to further improve the identification accuracy rate of weak positives, in this embodiment, the identification method for the detection results (antigen detection results) of the immunoreagent card further includes Step S80, i.e., optimizing the grayscale statistical threshold K and the brightness equalization coefficient β based on the nucleic acid detection results. This step includes:

Step S801, based on nucleic acid detection results fed back by the user, obtaining immunoreagent cards whose nucleic acid detection results are inconsistent with the identified immune result (antigen result) to form a first sample set; obtaining immunoreagent cards whose target area's chromaticity is near the grayscale statistical threshold K and whose nucleic acid detection results are consistent with the identified immune result to form a second sample set.

Step S802, dividing the first sample set and the second sample set into a uniform sample set and a non-uniform sample set separately according to immunoreagent card identification codes and equalization identification formed in a detection process of the non-uniform area. For the samples subjected to brightness equalization processing of the target detection area by using Step S40, a system will generate equalization identification. A marker bit can be used as equalization identification during identification operation; for example, a marker bit being 1 indicates that the samples have been subjected to equalization processing; a marker bit being 0 indicates that the samples have not been subjected to equalization processing.

Step S803, optimizing the grayscale statistical threshold K based on the uniform sample set of the first sample set and the uniform sample set of the second sample set. It can be obtained from the above data table that compared with a large number of negative samples, the number of samples in the first sample set is relatively small; correspondingly, the number of uniform samples in the first sample set is also relatively small. In order to increase the number of optimized samples, in this embodiment, detection images of the immunoreagent cards whose chromaticity is near the grayscale statistical threshold K and whose nucleic acid detection results are consistent with the identified antigen result are determined as the second sample set. During optimization, the uniform sample set of the first sample set is preferentially used for optimizing the grayscale statistical threshold K; then uniform samples of the second sample set are used for re-optimization for optimization verification.

Step S804, optimizing the brightness equalization coefficient (3 according to the optimized grayscale statistical threshold K, the non-uniform sample set of the first sample set, the non-uniform sample set of the second sample set and a grayscale dispersion parameter of the target area after equalization processing. Similarly, in this step, non-uniform samples of the first sample set are preferentially used for optimizing the brightness equalization coefficient β; then non-uniform samples of the second sample set are used for re-optimization for optimization verification.

In this embodiment, Step S401 is to detect the non-uniform area in the target area based on the variance of the grayscale value in the sliding window A (x, y). However, the present invention does not make any limitation to this. Although the identification accuracy rates of weak positives and negatives based on deep learning are not ideal, in Step S40, the characteristic parameters of the uniform area and the non-uniform area are obvious, so in other embodiments, the convolutional neural network can also be used for non-uniform area detection and brightness equalization. At the same time, the non-uniform samples of the first sample set and the second sample set can also be expanded into a training sample set of the convolutional neural network.

In addition to realizing the scale transformation of the image area of the immunoreagent card and the binding of the identified immune results by the identification code on the immunoreagent card, the automatic identification method for the detection results of the immunoreagent card provided by the present embodiment further includes Step S20 between Step S10 and Step S30, i.e., conducting tamper-proof verification on the uploaded immunoreagent card based on the identification code. Specifically, after an identification code representing an identity of a current immunoreagent card is identified, whether the current immunoreagent card is repeatedly uploaded is judged based on the serial number corresponding to the identification code; if the current immunoreagent card is repeatedly uploaded, then whether a last identification result of the immunoreagent card is abnormal is judged; if the last identification result is abnormal, the immunoreagent card is re-identified and a result of re-identification is bound to the serial number corresponding to the identification code. Abnormal identification result refers to special situations such as blank control area, detection area being blocked, or control area being blocked in the detection image of the obtained immunoreagent card in the last identification process. The tamper-proof verification based on the identification code and the last identification result can effectively prevent the behavior of tampering with the detection image of the immunoreagent card in order to obtain a negative result, and ensure the authenticity of identification.

Figure 6:
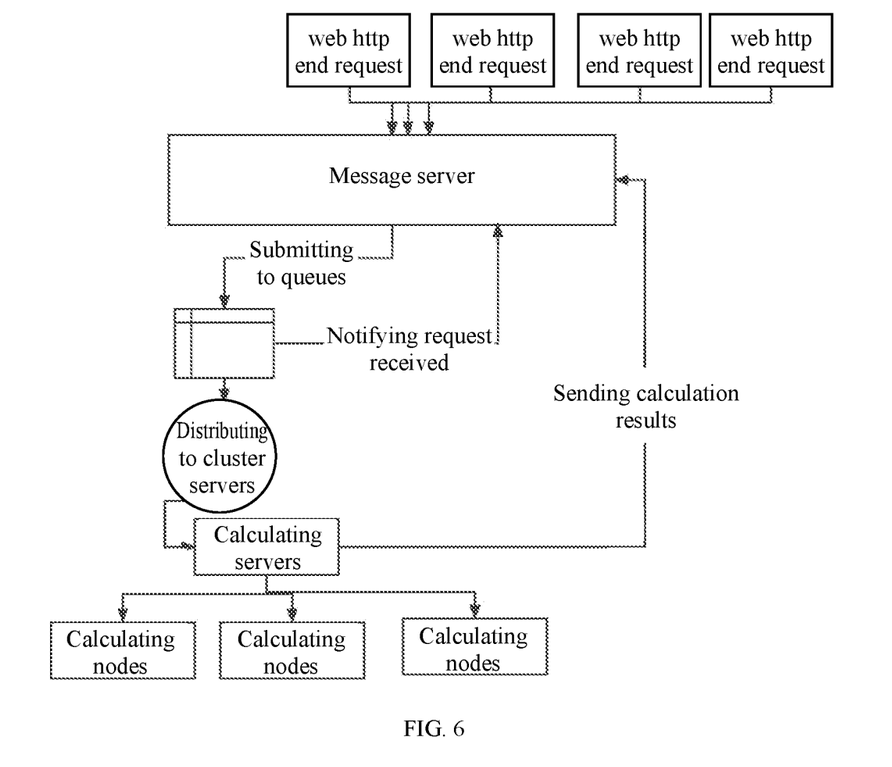
FIG. 6 shows a network block diagram of distributing and identifying immunoreagent card detection images by an identification device for detection results of an immunoreagent card of an embodiment of the present invention.

In the automatic identification method for the detection results of the immunoreagent card provided by the present embodiment, rapid judgment of negatives and moderate and strong positives based on the central area A1 greatly improves the identification rate. However, since the user uploads the detection image of the immunoreagent card and obtains the immune results of automatic identification through the web network, the overall identification speed will be affected by the transmission of the detection image of the immunoreagent card and the return of the identified immune results during identification. In addition, during large-scale antigen detection, the number of detection images of immunoreagent cards will be very large. In order to improve the speeds of invoking the immunoreagent card images and returning the identified immune results, the automatic identification method for the detection results of the immunoreagent card provided by the present embodiment, during obtaining the detection image of the immunoreagent card, further includes:

receiving a detection image of an immunoreagent reagent card photographed and uploaded by a user, and storing the detection image in a database server after the detection image is bound with an immunoreagent card serial number; sending a plurality of detection image information to a plurality of identification nodes in a manner of intranet in-turn distribution by a queue form, the detection image information including the immunoreagent card serial number corresponding to the detection image of the immunoreagent card; and querying the database server by the identification nodes based on a received immunoreagent card serial number to obtain the detection image of the immunoreagent card corresponding to the immunoreagent card serial number, identifying the detection image to obtain an identified immune result of the immunoreagent card, and binding the identified immune result with the current immunoreagent card serial number. That is, in the process of detection task allocation, the detection image information including the immunoreagent card serial number is always transmitted, and the content of a message body is smaller than the size of an HTTP packet, so the speed of detection task allocation is very high. In addition, a processing program is written in a compiled language (similar to C language), and the execution speed of the program is also very high.

In this embodiment, the plurality of identification nodes are paralleled, and a plurality of parallel computing nodes are dynamically expanded under each of the plurality of identification nodes, and each of the identification nodes distributes the detection image information to the plurality of computing nodes under there in a manner of in-turn distribution. A network topology structure in which the plurality of identification nodes are paralleled and the plurality of computing nodes are paralleled greatly facilitates the dynamic expansion of the identification nodes and the computing nodes, thereby meeting the needs of large-scale antigen detection. In this embodiment, the identification nodes are computing servers, and a plurality of parallel computing nodes (i.e., computer devices) are distributed under each of the computing servers.

Specifically, a message server connects to a client through a short connection http request, quickly receives the detection image of the immunoreagent card uploaded by the user, saves the detection image in the database server, and replies "request received". Then, the message server asynchronously distributes the detection image information to the multiple computing servers (i.e., identification nodes) in turn in a manner of licensing. Each of the computing servers also sends the detection image information to the computing node under there in a manner of licensing. The computing node obtains the corresponding immunoreagent card detection image from the database server located in the same network through a single-point tcp long connection based on the serial number in the detection image information. The detection image of the immunoreagent card is identified and the identification results are summarized to sending queues. The sending queues are sent to the message server one by one through a sending thread to provide the user with query results.

Figure 7:
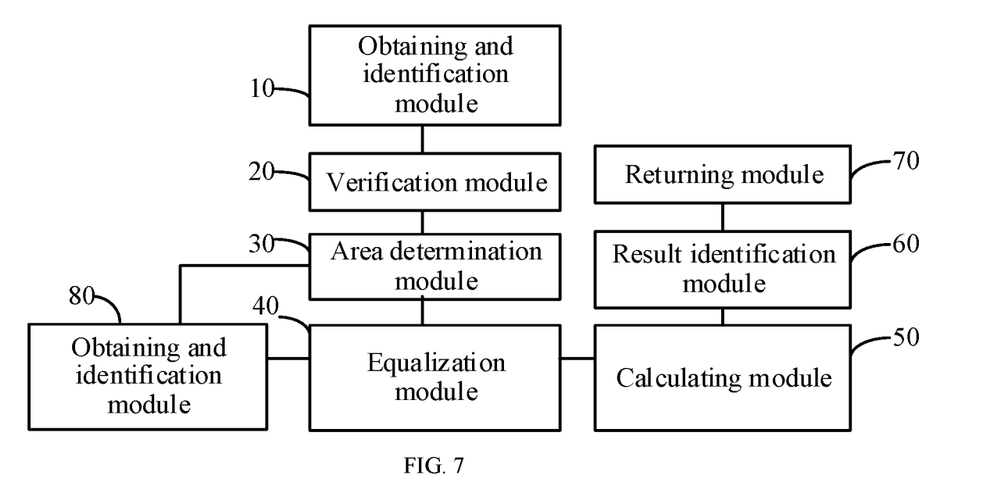
FIG. 7 shows a schematic structural diagram of an automatic identification apparatus for detection results of an immunoreagent card provided by an embodiment of the present invention.

Corresponding to the automatic identification method for the detection results of the immunoreagent card above, the present embodiment further provides an automatic identification apparatus for detection results of an immunoreagent card located on each computing node, including an obtaining and identification module 10, a verification module 20, and an area determination module 30, an equalization module 40, a calculating module 50, a result identification module 60, a returning module 70 and an optimizing module 80. The obtaining and identification module 10 identifies a detection character and an identification code on a detection image of an obtained immunoreagent card. The verification module 20 conducts tamper-proof verification on the uploaded immunoreagent card based on the identification code. The area determination module forms a corresponding target area based on the detection character, determines a central sub-area in the target area and calculates histogram information of the central sub-area. The equalization module 40 detects a non-uniform area in the target area when the histogram information of the central sub-area is between a minimum grayscale statistical threshold and a maximum grayscale statistical threshold, scans the non-uniform area line by line, and conducts brightness equalization processing on a pixel value of each pixel point on a scanning line based on a brightness equalization coefficient. The calculating module 50 identifies an edge of a detection line of the target area after equalization processing, and calculates the histogram information. The result identification module 60 determines a chromaticity of the target area through an approximate linear relationship based on a grayscale statistical threshold and the calculated histogram information, and forms an immune result of automatic identification of the immunoreagent card according to the chromaticity of the target area corresponding to each detection character. The returning module 70 binds the identified immune result of the immunoreagent card with a serial number corresponding to the identification code of the immunoreagent card, and returns the identified immune result bound with the serial number to a user when receiving a user's query request based on the serial number. The optimizing module 80 optimizes the grayscale statistical threshold K and the brightness equalization coefficient $\beta$ based on the identified immune result and nucleic acid detection results, and optimizes the central area A1 based on non-uniform area detection.

Since respective functions of the automatic identification apparatus for the detection results of the immunoreagent card have been described in detail in the corresponding method steps S10 to S80, they will not be repeated here.

Figure 8:
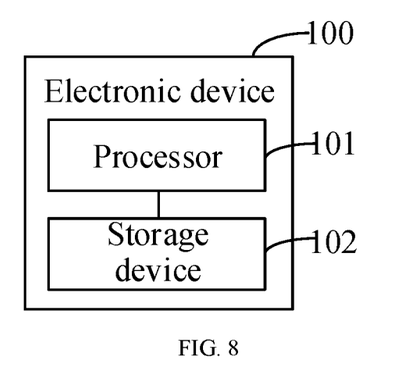
FIG. 8 shows a schematic structural diagram of an identification device for detection results of an immunoreagent card provided by an embodiment of the present invention.

FIG. 8 shows a schematic structural diagram of a computing node in this embodiment, where the computing node is an electronic device. It needs to be noted that the electronic device shown in FIG. 8 is only an example, and should not impose any limitation on the functions and scope of use of the embodiments of the present disclosure. The electronic device 100 includes one or more processors 101 and a storage device 102. The storage device 102 is used for storing one or more programs. When the one or more programs are executed by the one or more processors 101, the one or more processors 101 are caused to implement the automatic identification method for the detection results of the immunoreagent card provided by the present embodiment.

To sum up, in the automatic identification method, apparatus and device for the detection results of the immunoreagent card provided by the present invention, judgment of negatives and strongly positives can be quickly realized based on the judgment of the histogram information in the central sub-area, thereby greatly improving an identification rate. For the histogram information of the central sub-area between the minimum grayscale statistical threshold and the maximum grayscale statistical threshold, brightness equalization is conducted on the target region to compensate for interference with the histogram information by an uneven brightness caused by photographing by the user, so that an identification accuracy rate can be greatly improved, and dual-index requirements of large-scale antigen detection in terms of identification accuracy rate and identification speed can be well met.

In addition, both the optimization of the range of the central sub-area based on the detection of the non-uniform area of the target area and the optimization of the grayscale statistical threshold and the brightness equalization coefficient based on the multi-type sample sets expanded by identified immune results and nucleic acid detection results can further improve the accuracy rate and speed of identification.

Although the present invention has been disclosed above by preferred embodiments, it is not intended to limit the present invention. Anyone who is familiar with the art can make some changes and modifications without departing from the spirit and scope of the present invention. Therefore, the scope of protection of the present invention shall be subject to the scope of protection claimed by the claims.

The invention claimed is:

1. An automatic identification method for detection results of an immunoreagent card, comprising:
   identifying a detection character and an identification code on a detection image of an obtained immunoreagent card;
   forming a corresponding target area based on the detection character, determining a central sub-area in the target area and calculating histogram information of the central sub-area;
   detecting a non-uniform area in the target area when the histogram information of the central sub-area is between a minimum grayscale statistical threshold and a maximum grayscale statistical threshold, scanning the non-uniform area line by line, and conducting brightness equalization processing on a pixel value of each pixel point on a scanning line based on a brightness equalization coefficient;
   identifying an edge of a detection line of the target area after equalization processing, calculating the histogram information, and determining a chromaticity of the target area through an approximate linear relationship based on a grayscale statistical threshold and the calculated histogram information;
   forming an immune result of automatic identification of the immunoreagent card according to the chromaticity of the target area corresponding to the detection character; and
   binding the identified immune result with a serial number corresponding to the identification code of the immunoreagent card, and returning the identified immune result bound with the serial number to a user when receiving a user's query request based on the serial number.

2. The automatic identification method for the detection results of the immunoreagent card according to claim 1, wherein the step of determining the central sub-area in the target area and calculating the histogram information of the central sub-area comprises:
   dividing the target area into the central sub-area and a plurality of side sub-areas located on two sides of the central sub-area, and adaptively adjusting a range of the central sub-area based on a detection boundary of a non-uniform area of a historical immunoreagent card, the range of the central sub-area being greater than a sum of areas of all the side sub-areas;
   identifying an edge of a detection line of the central sub-area to obtain a histogram of the central sub-area; and
   conducting statistics on the histogram to obtain the histogram information.

3. The automatic identification method for the detection results of the immunoreagent card according to claim 1, further comprising:
   based on nucleic acid detection results fed back by the user, obtaining immunoreagent cards whose nucleic acid detection results are inconsistent with the identified immune result to form a first sample set; obtaining immunoreagent cards whose target area's chromaticity is near the grayscale statistical threshold and whose nucleic acid detection results are consistent with the identified immune result to form a second sample set;
   dividing the first sample set and the second sample set into a uniform sample set and a non-uniform sample set separately according to immunoreagent card identification codes and equalization identification formed in a detection process of the non-uniform area;
   optimizing the grayscale statistical threshold based on the uniform sample set of the first sample set and the uniform sample set of the second sample set; and
   optimizing the brightness equalization coefficient according to the optimized grayscale statistical threshold, the non-uniform sample set of the first sample set, the non-uniform sample set of the second sample set and a grayscale dispersion parameter of the target area after equalization processing.

4. The automatic identification method for the detection results of the immunoreagent card according to claim 3, wherein non-uniform area detection and brightness equalization are conducted in the target area by a convolutional neural network, and the non-uniform samples of the first sample set and the second sample set are expanded into a training sample set of the convolutional neural network.

5. The automatic identification method for the detection results of the immunoreagent card according to claim 1, wherein coordinates of a plurality of characteristic positions are determined on the detection character and the identification code separately after the detection character and the identification code are identified, and an image area where the immunoreagent card is located is transformed into a same scale by affine transformation based on the coordinates of the plurality of characteristic positions; and a preset pixel window is extended based on each detection character to form the target area corresponding to the detection character.

6. The automatic identification method for the detection results of the immunoreagent card according to claim 1, wherein after an identification code representing an identity of a current immunoreagent card is identified, whether the current immunoreagent card is repeatedly uploaded is judged based on the serial number corresponding to the identification code; if the current immunoreagent card is repeatedly uploaded, then whether a last identification result of the immunoreagent card is abnormal is judged; if the last identification result is abnormal, the immunoreagent card is re-identified and a result of re-identification is bound to the serial number corresponding to the identification code.

7. The automatic identification method for the detection results of the immunoreagent card according to claim 1, further comprising:
receiving a detection image of an immunoreagent reagent card photographed and uploaded by a user, and storing the detection image in a database server after the detection image is bound with an immunoreagent card serial number;
sending a plurality of detection image information to a plurality of identification nodes in a manner of intranet in-turn distribution by a queue form, the detection image information comprising the immunoreagent card serial number corresponding to the detection image of the immunoreagent card; and
querying the database server by the identification nodes based on a received immunoreagent card serial number to obtain the detection image corresponding to the immunoreagent card serial number, identifying the detection image to obtain an identification result of the immunoreagent card, and binding the identification result with the current immunoreagent card serial number.

8. The automatic identification method for the detection results of the immunoreagent card according to claim 7, wherein the plurality of identification nodes are paralleled, and a plurality of parallel computing nodes are dynamically expanded under each of the plurality of identification nodes, and each of the identification nodes distributes the detection image information to the plurality of computing nodes under there in a manner of in-turn distribution.

9. The automatic identification method for the detection results of the immunoreagent card according to claim 1, wherein the detection character comprises a character T or a character C.

10. The automatic identification method for the detection results of the immunoreagent card according to claim 9, wherein a target area corresponding to the character T is a detection area, and a target area corresponding to the character C is a control area for detection results.

11. The automatic identification method for detection results of the immunoreagent card according to claim 10, wherein an antibody to an analyte is immobilizes on the detection area.

12. The automatic identification method for detection results of the immunoreagent card according to claim 11, wherein the analyte is a corona virus.

13. The automatic identification method for detection results of the immunoreagent card according to claim 9, wherein the target area corresponding to the character T is in a form of a line.

14. The automatic identification method for detection results of the immunoreagent card according to claim 9, wherein the identified immune result is obtained based on the target area corresponding to the character T.

15. An automatic identification apparatus for detection results of an immunoreagent card, comprising:
an obtaining and identification module, configured for identifying a detection character and an identification code on a detection image of an obtained immunoreagent card;
an area determination module, configured for forming a corresponding target area based on the detection character, determining a central sub-area in the target area and calculating histogram information of the central sub-area;
an equalization module, configured for detecting a non-uniform area in the target area when the histogram information of the central sub-area is between a minimum grayscale statistical threshold and a maximum grayscale statistical threshold, scanning the non-uniform area line by line, and conducting brightness equalization processing on a pixel value of each pixel point on a scanning line based on a brightness equalization coefficient;
a calculating module, configured for identifying an edge of a detection line of the target area after equalization processing, and calculating the histogram information;
a result identification module, configured for determining a chromaticity of the target area through an approximate linear relationship based on a grayscale statistical threshold and the calculated histogram information, and forming an immune result of automatic identification of the immunoreagent card according to the chromaticity of the target area corresponding to the detection character; and
a returning module, configured for binding the identified immune result with a serial number corresponding to the identification code of the immunoreagent card, and returning the identified immune result bound with the serial number to a user when receiving a user's query request based on the serial number.

16. The automatic identification apparatus for the detection results of the immunoreagent card according to claim 15, wherein the detection character is a character T, and a target area corresponding to the character T is a detection area.

17. The automatic identification apparatus for the detection results of the immunoreagent card according to claim 16, wherein the analyte is a corona virus.

18. The automatic identification apparatus for the detection results of the immunoreagent card according to claim 15, wherein the detection area is in a form of a line.

19. The automatic identification apparatus for the detection results of the immunoreagent card according to claim 15, wherein an antibody to an analyte is immobilizes on the detection area.

20. An electronic device, comprising:
one or more processors; and
a storage device for storing one or more programs,
wherein when the one or more programs are executed by the one or more processors, the one or more processors are caused to implement the automatic identification method for the detection results of the immunoreagent card according to claim 1.

* * * * *